United States Patent [19]
Vogelman et al.

[11] 3,958,570
[45] May 25, 1976

[54] SYRINGES AND SYRINGE CAPSULES

[76] Inventors: Joseph H. Vogelman, 48 Green Drive, Roslyn, N.Y. 11576; Norman Orentreich, 140 E. 72nd St., New York, N.Y. 10021

[22] Filed: Sept. 3, 1974

[21] Appl. No.: 502,599

[52] U.S. Cl. ................. 128/218 DA; 128/218 P; 128/234
[51] Int. Cl.² ........................................ A61M 5/00
[58] Field of Search ........ 128/218 P, 218 R, 218 D, 128/218 DA, 234, 218 C, 218 G, 218 M

[56] References Cited
UNITED STATES PATENTS

| | | | |
|---|---|---|---|
| 2,561,233 | 7/1951 | Ryan et al. | 128/218 D |
| 2,607,342 | 8/1952 | Abel | 128/218 P |
| 2,735,735 | 2/1956 | Abel | 128/218 P X |
| 2,761,447 | 9/1956 | Hersee | 128/218 M |
| 2,842,127 | 7/1958 | Everett | 128/218 P |
| 2,933,087 | 4/1960 | Hamilton | 128/221 |
| 3,026,872 | 3/1962 | Prater, Jr. | 128/218 P |
| 3,110,309 | 11/1963 | Higgins | 128/218 D |
| 3,150,801 | 9/1964 | Hamilton | 128/218 R X |
| 3,366,113 | 1/1968 | Hobbs | 128/218 D |
| 3,566,859 | 3/1971 | Schwartz | 128/218 M |
| 3,730,389 | 5/1973 | Harris, Sr. et al. | 128/234 X |

*Primary Examiner*—John D. Yasko
*Attorney, Agent, or Firm*—Nolte and Nolte

[57] ABSTRACT

In a syringe or syringe capsule, particularly for microadministration of highly viscous liquids, there are provided a zero or negative allowance between the barrel and the plunger and a low friction, resilient interface between the barrel and the plunger. There is thus provided a high pressure-resistant seal which, nevertheless, permits manual operation of the syringe with a reasonable amount of force.

11 Claims, 6 Drawing Figures

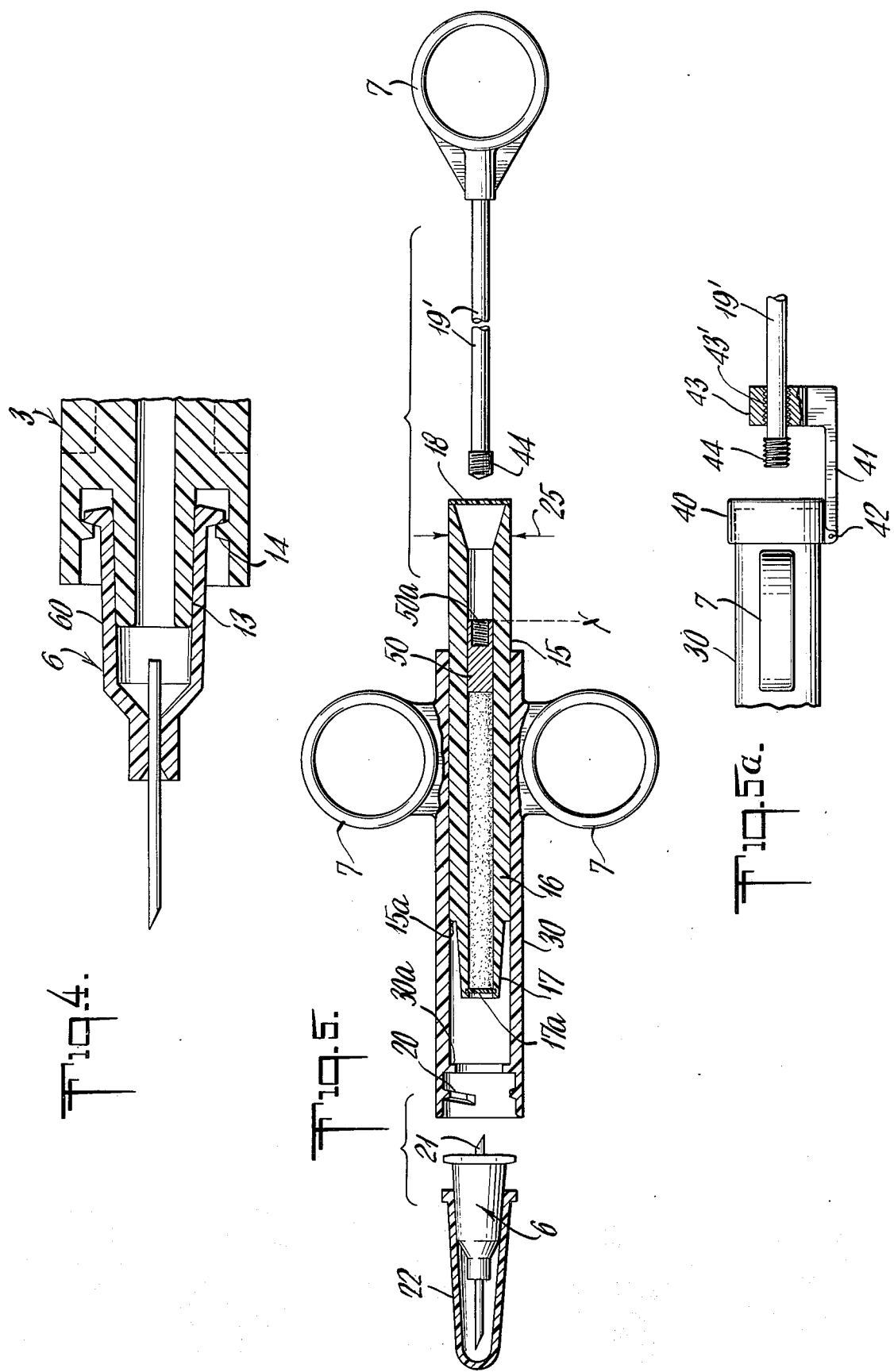

SYRINGES AND SYRINGE CAPSULES

This invention relates to hypodermic syringes and more particularly to a high pressure microsyringe suitable for micro-administration of a highly viscous substance.

Prior art hypodermic syringes are generally of the type having a glass barrel and either a glass or metal plunger. Such prior art syringes employ various sealing techniques, such as providing the plungers with rubber rings. Seals of this kind are quite adequate for low viscosity substances, which i n turn require low pressure in their administration. U.S. Pat. No. 3,628,523 (Pirtle, Jr.) shows one such syringe in which a stainless steel plunger coated with Teflon (Teflon is a registered trademark of DuPont Corporation for fluorinated hydrocarbon resins) is inserted into a syringe barrel formed of glass. However, such prior art syringes are inadequate for high pressure micro-applications, in that the barrel cracks and/or the syringes develop other leaks. This is especially true when the substance to be administered is of a highly viscous nature.

It is, therefore, an object of this invention to provide a syringe seal capable of maintaining a high pressure.

It is a further object of this invention to provide a high pressure syringe or syringe capsule for micro-administration of a highly viscous substance.

This invention relates, therefore, to a micro-syringe capable of high pressure micro-administration of a highly viscous liquid such as a silicone liquid. The high pressure required is maintainable due to a unique seal formed between the syringe's plunger and barrel, i.e., zero or negative allowance is maintained between the barrel and the plunger, but the plunger is, nevertheless, receivable and slidable in the barrel under application of an amount of force that can conveniently be applied in manual operation of the plunger. This is accomplished by so constructing the syringe barrel and the syringe plunger that their interface is resilient and of low friction. When comparing the diameter of the barrel and the plunger, it is to be understood that relaxed, unstressed diameters are being referred to and that a larger diameter plunger can be manually slidably received in a smaller diameter barrel due to the resiliency of and low friction between the materials employed.

In a preferred embodiment, the syringe barrel is formed from a resilient, preferably transparent or transsluscent, plastic such as a polypropylene, a polyethylene or other similarly resilient plastic, having a resiliency selected according to the sealing pressure characteristics desired, and the syringe plunger is formed by coating a rigid rod of a sufficiently strong material such as steel or an engineering plastic, e.g., linear polyoxymethylene acetal resin, with a low friction material such as a fluorinated hydrocarbon resin or a silicone resin or any other similarly low friction, preferably resilient, material. In this last regard, however, it must be emphasized that, should a silicone resin be used as the coating, a silicone resin must be selected which will not react or combine with the liquid silicone to be administered.

In the case of a syringe capsule, i.e., a factory sealed capsule containing the liquid to be administered and designed for use together with a capsule holder, plunger and needle as a syringe, the needle optionally being integral with the capsule as part of the unit assembled in the factory and the capsule optionally being manufactured with a completely internal plunger which is operated by insertion of an auxiliary plunger when the liquid is to be administered, the same principle of the present invention applies, since the capsule functionally constitutes the syringe barrel.

The barrel or capsule may be fabricated of a rigid material (e.g., a glass, metal or engineering plastic) coated on its inner diameter surface with the low friction material and the plunger or plungers may be coated with the resilient plastic (e.g., a polyethylene or polypropylene). This is less preferred, however. Apart from the fact that the barrel or capsule would be completely opaque whereby the extent of discharge from the syringe would not be visible unless a longitudinal viewing slit was provided, coating of the inner diameter surface of the barrel or capsule would make the syringe or capsule more expensive. While the barrel or capsule may be made entirely of fluorinated hydrocarbon resin, the barrel or capsule would be less resilient and more expensive than a barrel or capsule of resilient plastic such as polypropylene, polyethylene or the like. A plunger contained in the capsule may be made of fluorinated hydrocarbon resin. However, a longer plunger for operation from a point external to the syringe barrel or capsule and in an extended position not being surrounded by structure preventing it from bending, if made entirely of fluorinated hydrocarbon resin and of a small diameter suitable for a syringe for micro-administration would tend to be deficient in mechanical strength.

Gripping rings may be provided on the capsule holder and plunger for facilitating a tight grip, thus enabling one to push the plunger with considerable force.

In order that the invention will be more clearly understood, it will now be described in greater detail with reference to the accompanying drawings, wherein:

FIG. 4 is a detail of a fragment of FIG. 3 and shows a standard Luer taper and lock for connecting a needle to the syringe;

FIG. 5 is a side elevation, partly in section, of a partly assembled capsule syringe suitable for high pressure micro-administration of a highly viscous substance; and FIG. 5A is a fragmentary side elevation of a combination of the capsule of FIG. 5 with a plunger hingedly connected to the capsule.

Figure 1:
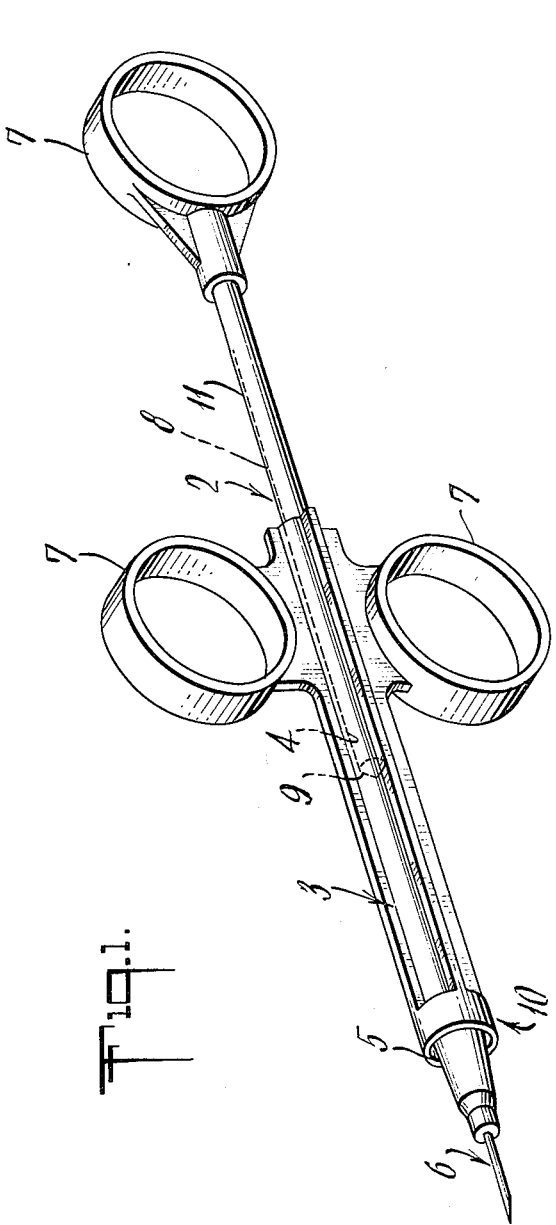
FIG. 1 is an isometric view of a hypodermic syringe of the invention suitable for the administration of a highly viscous substance.

In accordance with this invention, FIG. 1 shows a high pressure microsyringe suitable for delivery of 0.25 cubic centimeter of a high viscosity liquid, such as a silicone, in 0.01 to 0.02 cubic centimeter doses. A high pressure seal is formed between the syringe plunger 2 and the syringe barrel 3 because a zero or negative allowance is provided between the plunger 2 and the barrel 3. The plunger 2 is made of stainless steel and is coated with a low friction material such as Teflon. The barrel 3 is made from a resilient plastic (polypropylene), and has an inner diameter 4 equal to or less than the diameter of the Teflon coated plunger 2. The syringe barrel 3 has a Luer lock 5 with an internal Luer taper, for connecting a 30 gauge needle 6 to the barrel 3. Gripping rings 7 are provided on the barrel 3 and plunger 2 for facilitating a tight grip to enable one to push the plunger with considerable force. The advantage of gripping rings is further explained in U.S. Pat. No. 2,568,173, (Spivack), which shows gripping rings on the barrel and plunger of a standard syringe.

Figure 2:
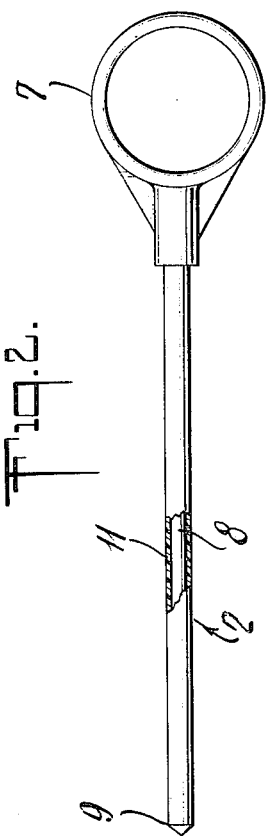
FIG. 2 is a side elevation of a coated stainless steel plunger forming part of the syringe of FIG. 1.

FIG. 2 shows a Teflon coated stainless steel plunger 2 which, in combination with a resilient plastic barrel 3 as described with reference to FIG. 3, forms a high pressure syringe as described in FIG. 1. The plunger core or center 8 is a 0.079 inch diameter stainless steel rod 2 for providing mechanical strength and rigidity. The rod 2 is Teflon coated 11 over a length of 3 ½ inches beginning at the end 9 to form a coated plunger of 0.080 inch or slightly greater diameter. A gripping ring 7 is fastened to the other end of the rod 2.

Figure 3:
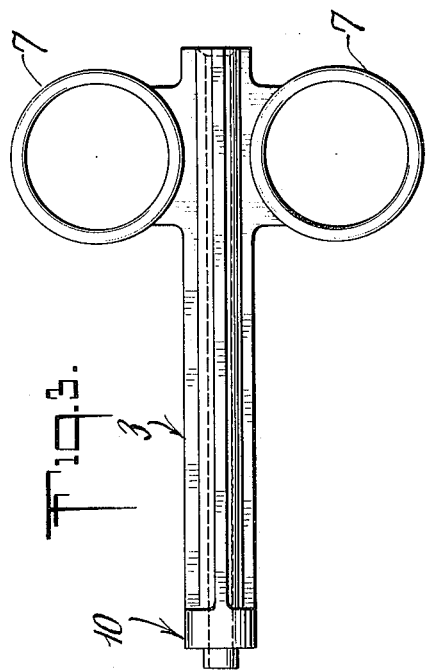
FIG. 3 is a side elevation, partly in section, of a syringe barrel for use with the plunger illustrated in FIG. 2.

FIG. 3 shows in accordance with this invention a resilient plastic barrel 3, which in combination with the coated syringe plunger of FIG. 2 forms the syringe as illustrated in FIG. 1. The barrel 3 is 4 inches in length and formed of resilient, transluscent plastic (polypropylene). A 0.080 inch diameter bore is formed at the center of the barrel and traverses its length. Gripping rings 7 are connected to, or formed as part of, the barrel 3 to facilitate a tight grip. A standard Luer taper and lock combination 10 is formed at the other end of the barrel 3 for connecting a needle to the syringe.

As seen in FIG. 4, a standard Luer taper 13 and Luer lock 14 connects the needle 6 to the syringe. The needle 6 is provided with a base 60 which is tapered to mate with the Luer taper 13, thereby forming a seal between the needle 6 and the syringe 3, as the needle 6 is locked by means of the Luer lock 14.

FIG. 5 shows another embodiment of this invention, in which a high pressure capsule type syringe is provided for delivery of 0.25 cubic centimeter of a high viscosity silicone liquid, through a 30 gauge needle in 0.01 to 0.02 cubic centimeter doses. The capsule type syringe is comprised of a holder 30, a first plunger 19′ having a threaded end 44, and a capsule 15. The holder 30 can be made from any suitably rigid substance, such as a glass, metal, or plastic, preferably transparent or transluscent or provided with a longitudinal viewing slot, having an inner diameter larger than the outer diameter 25 of the capsule 15. The capsule 15 is inserted into the holder 30, thereby being supported and housed by the holder 30. The capsule 15 is formed from a resilient plastic. A gripping ring 7 is provided at one end of the plunger (19′) for facilitating a tight grip. Gripping rings 7 are also provided on the holder 30. The holder 30 further has a Luer lock 20 and one end of the capsule is in the form of a Luer taper 17 for the connection of a needle.

The capsule containing silicone liquid or other substance to be administered is inserted, tapered end 17 first, into the holder 30 until the annular shoulder 15a formed on the capsule 15 engages the annular lip 30a formed in the holder 30. Next, a two-ended needle 6 is connected to the holder 30 by means of the Luer lock 20, whereby a needle end 21 would pierce and be inserted into end wall 17a of the tapered end 17 of the capsule 15. As sold, the needle 6 is provided with a cover 22, which may conveniently be of plastic, for example, and is manually removably press fit onto the base 60 of the needle 6.

The capsule 15 has an inner diameter to the left of point X of 0.080 inches, for receiving therein the syringe plunger 50 of 0.080 inch or slightly greater diameter. To the right of point X, the diameter decreases to 0.075 inch, for example, and received therein is a second plunger 19′ of a diameter of 0.065 inch or slightly less. The plunger 50 is coated with Teflon or other low friction material as is the plunger 2 of the embodiment of FIGS. 1 through 3 and is provided with a threaded bore 50a for receiving the threaded end 44 of the plunger 19′. This threaded connection enables aspiration of blood into the syringe or pulling back of the plunger 50 for any other purpose after the plunger 50 has been pushed forward. In the factory, the capsule has been filled with the liquid to be administered, such as silicone, at the tapered end 17 and heat sealed in sterile condition. The annular shoulder formed at X by the change in diameter retains the plunger 50 as a seal for the liquid contained in the capsule. The capsule is also sealed by a plastic membrane 18 which is scribed with an X so that it will break at the center upon the insertion of the plunger (19′).

The plunger 19′ may be sold as a unit with the holder 30; it may be convenient to hingedly connect the plunger 19′ to the holder 30 so that, to permit compact packaging, the plunger would be arranged parallel to the holder 30 when not in use and would be swung into axial alignment with and inserted into the capsule when the capsule contents were to be administered. An exemplary hinging arrangement is illustrated in FIG. 5A, in which 40 is a metal or plastic band tightly engaging the holder 30 to which band an arm 41 is pivotally connected by means of a pivot pin 42 and rigidly connected to the other end of the arm 41 is a sleeve 43 in which slidably mounted is the plunger 19′. As illustrated, the plunger 19′ is axially aligned with the holder 30 after the capsule 15 is inserted in the holder 30. The plunger 19 is now ready for insertion into plunger 50. It will be appreciated that a counter-clockwise rotation of 180° would bring the plunger 19′ into a position alongside the holder 30 and the hingedly connected holder 30 and plunger 19′ would be packaged in that more compact configuration. The end 44 of the plunger 19′ to be inserted into the capsule 15 is threaded as it also is in FIG. 5. The sleeve 43 is provided with internal threads 43′ which mate with the threads at the end 44 of the plunger 19′. When the plunger 19′ is first inserted in the sleeve 43, it is twisted until the threaded end 44 has been screwed past the threads 43′. Hence, the plunger 19′ cannot be withdrawn from the sleeve 43 without being twisted in the opposite direction when the respective threads engage. This prevents accidental separation of the plunger 19′ from the sleeve 43. Desirably, the diameter of the plunger 19′ other than at the threaded end 44 is similar to the crest diameter of the threads 43′ so that after the plunger is captured by the interaction of the threads, the threads 43′ serve to guide and support the plunger 19′ in its sliding movement.

It is to be recognized that, although applicant has particularly described this invention by reference to specific preferred embodiments, this invention may be in the form of other embodiments which are to be considered to be within the scope of the invention as defined by the appended claims. Thus, for example, the capsule may be formed with the needle integral therewith; in that case, a sealing membrane may be provided in the interior of the capsule adjacent the end of the needle within the capsule, which membrane is rupturable, by provision of score lines for example, by the pressure exerted on the liquid by the plunger 50 upon manual plunging of the plunger 19. Another variation is that a rubber piston may be provided on the end of the plunger rod as a secondary seal; this, however, is not necessary for an adequate sealing.

What is claimed is:
1. A syringe comprising:
a resilient plastic barrel having a predetermined inner diameter; and
received in the barrel a plunger having a metal core of lesser diameter than the inner diameter of the barrel and a coating of a resilient, low friction material, the diameter of the coating being greater than the barrel's inner diameter, the plunger being manually slidable in the barrel, the coating extending continuously along the plunger from the distal end of the plunger to at least that part of the plunger most remote from the distal end but received in the barrel when the plunger is slid down to the bottom of the barrel, whereby the syringe is adapted to exert high pressure without leakage.

2. A syringe according to claim 1, wherein:
the barrel is formed from polypropylene or polyethylene.

3. A syringe according to claim 2, wherein:
the plunger is coated with a poly(fluorinated hydrocarbon) resin or a silicone resin.

4. A syringe according to claim 2, wherein:
the plunger is stainless steel coated with a poly(fluorinated hydrocarbon) resin.

5. A syringe according to claim 1, wherein:
the capacity of the barrel is 0.25 to 1.0 cubic centimeter.

6. In combination, a syringe capsule and a syringe plunger received in the syringe capsule, the syringe capsule having an outer diameter predetermined for insertion into a syringe holder, an inner diameter predetermined for receiving therein the syringe plunger, and an end adapted for receiving a needle, the capsule being constituted of a resilient plastic and the plunger being constituted of a metal core of lesser diameter than the inner diameter of the capsule and a coating of a resilient, low friction material, the diameter of the coating being greater than the capsule's inner diameter, the plunger being manually slidable in the barrel, the coating extending continuously along the plunger from the distal end of the plunger to at least that part of the plunger most remote from the distal end but received in the barrel when the plunger is slid down to the bottom of the barrel, whereby the combination is adapted to exert high pressure without leakage.

7. In combination, a syringe capsule comprising a resilient plastic body having an outer diameter predetermined for insertion into a syringe holder, an inner diameter along a first part of its length for receiving therein a syringe plunger extending externally of the capsule and a larger inner diameter along a second part of its length, a metal syringe plunger received in the first part of the length of the body and extending externally of the capsule and an additional plunger received entirely within the second part of the length of the body, said additional plunger being constituted of a resilient, low friction material continuously along its entire length, being of diameter greater than the diameter of the second part of the length of the body and being slidable within the second part of the length of the body upon manual actuation of the externally extending plunger and engagement of the additional plunger by the thus actuated externally extending plunger, the additional plunger being provided with a threaded bore, the distal end of the first plunger being threaded and being engaged completely in the bore in the additional plunger by mating of the respective threads so that the additional plunger completely surrounds the first plunger, whereby the syringe capsule is adapted to exert high pressure without leakage.

8. A syringe capsule adapted to be mounted in a holder and containing in a sertile condition a substance to be administered, said capsule comprising a resilient plastic body having a cavity of a predetermined diameter, a sterile substance to be administered contained in the cavity, a plunger slidably received in a portion of the hollow body communicating with the cavity, the plunger having a metal core of lesser diameter than the cavity and continuously along its length a coating of a resilient, low friction material, the diameter of the coating being greater than the predetermined diameter of the cavity and the plunger being slidably receivable in the cavity, means sealing off from the ambient, the cavity, the substance contained in the cavity and the plunger, said sealing means comprising a rupturable seal proximate to one extremity of the capsule, said one extremity being adapted to be in engagement with a syringe needle, and a seal proximate to the opposite extremity of the capsule and adapted to be ruptured by means for engaging the plunger contained in the capsule for urging the plunger into the cavity to force the substance from the cavity through a needle piercing said seal at said one extremity of the capsule when the substance is to be administered, whereby the syringe capsule is adapted to exert high pressure without leakage.

9. A syringe capsule according to claim 8, in which said means for engaging the plunger comprises an additional plunger having a threaded end for engaging the plunger contained in the capsule and the plunger contained in the capsule has a threaded hole for receiving said threaded end whereby the additional plunger can be actuated to move the plunger contained in the capsule either toward or away from the needle when the substance is to be administered.

10. In combination, a syringe capsule according to claim 8, and a holder in which combination said means for engaging the plunger comprises an additional plunger, and further comprising means for connecting said additional plunger to said holder for ready availability of said additional plunger and for permitting said additional plunger to be inserted into the capsule while still so connected.

11. The combination of claim 10, in which said connecting means comprises hinge means.

* * * * *